United States Patent [19]

Wachinski et al.

[11] Patent Number: 4,637,528

[45] Date of Patent: Jan. 20, 1987

[54] ARTICULATED JOINT IN AEROSOL MEDICAMENT DISPENSER

[75] Inventors: Clarence A. Wachinski, Abington; Thomas J. Bigger, Perkasie, both of Pa.

[73] Assignee: William H. Rorer, Inc., Fort Washington, Pa.

[21] Appl. No.: 572,292

[22] Filed: Jan. 19, 1984

[51] Int. Cl.[4] .............................................. B65D 83/14
[52] U.S. Cl. ................................ 222/182; 222/402.12; 128/200.23; 16/361
[58] Field of Search ...................... 128/200.23, 203.15; 16/360, 361, 363, 364, 374, 379, 380, 381, 386; 222/164, 166, 402.11, 402.12–402.13, 522–525, 529, 530, 533, 536, 538, 566–576; 403/117; 239/337, 587

[56] References Cited

U.S. PATENT DOCUMENTS

| | | | |
|---|---|---|---|
| 177,835 | 5/1876 | Hempleman | 403/117 |
| 827,950 | 8/1906 | Zimmer | 403/117 X |
| 2,498,558 | 2/1950 | Lantz | 16/374 X |
| 2,737,311 | 3/1956 | Blacher | 16/374 X |
| 3,184,115 | 5/1965 | Meshberg | 128/200.23 X |
| 3,236,458 | 2/1966 | Ramis | 128/200.23 X |
| 3,478,931 | 11/1969 | Lynn | 222/166 |
| 3,927,806 | 12/1975 | Meshberg | 222/402.12 |
| 3,994,421 | 11/1976 | Hansen | 222/182 |

FOREIGN PATENT DOCUMENTS 2110543 6/1983 United Kingdom ........... 128/200.23

Primary Examiner—Charles A. Marmor
Assistant Examiner—Michael S. Huppert
Attorney, Agent, or Firm—James A. Nicholson; Charles H. Lindrooth

[57] ABSTRACT

A sliding and pivoting joint, and a retractable medicament spray dispenser having such a joint. A sleeve is telescopically mounted on the dispenser housing by engaging a pair of pin-like projections on a pair of ears on the sleeve into slots which are in opposite side walls of the housing. An elongated stud protrudes perpendicularly from the inward end of each pin. When the sleeve has been telescopically extended relative to the housing, abutments in the housing interact with the protruding studs to prevent the sleeve from being pivoted to any positions beyond those which correspond to the storage and the operating configurations of the dispenser.

5 Claims, 10 Drawing Figures

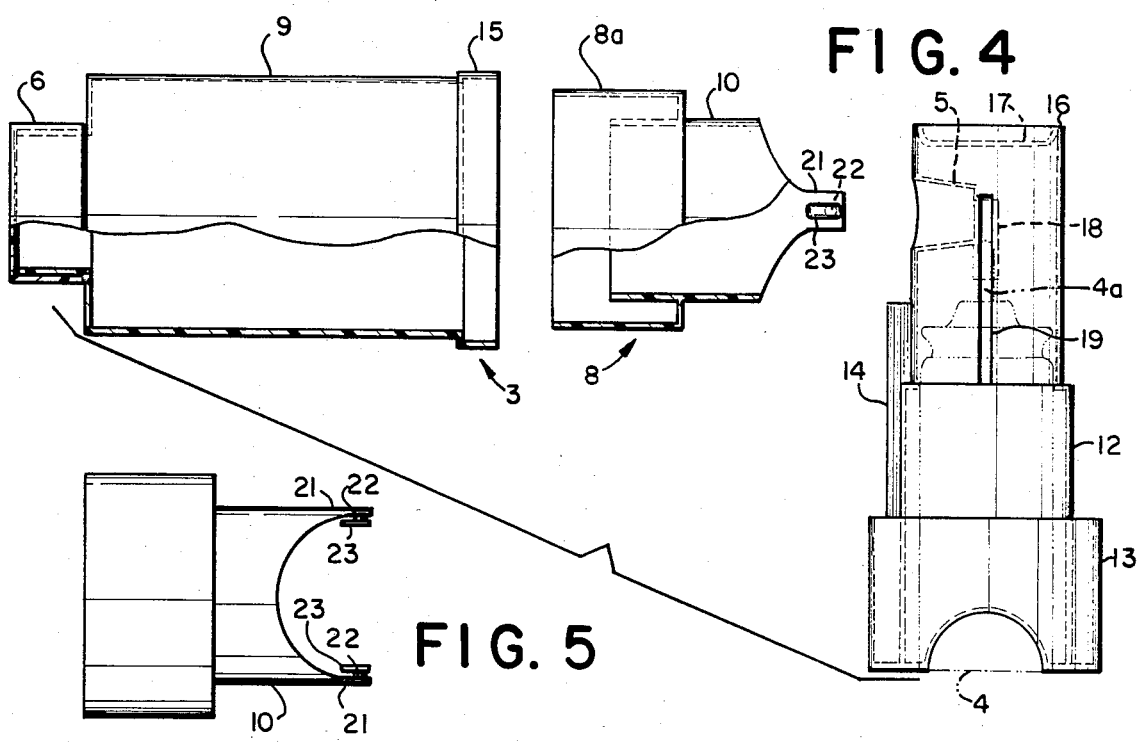
FIG. 4
FIG. 5
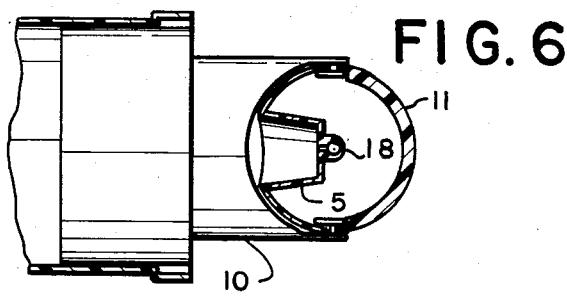
FIG. 6
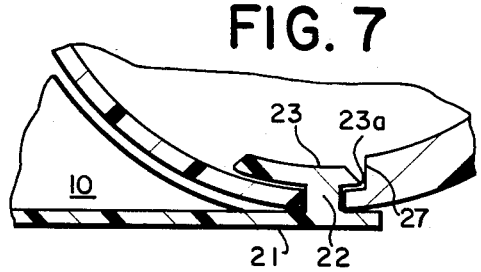
FIG. 7
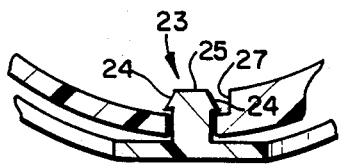
FIG. 8
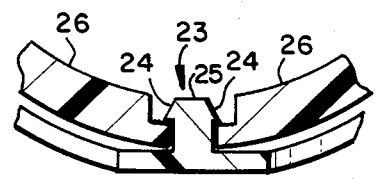
FIG. 9
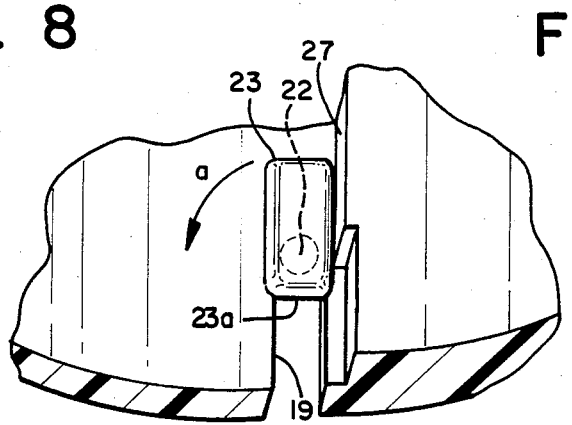
FIG. 10

ARTICULATED JOINT IN AEROSOL MEDICAMENT DISPENSER

FIELD OF THE INVENTION

This invention relates to a telescoping and pivoting joint, and to the provision of such a joint in an aerosol dispenser of the type for spraying a measured amount of medicament for inhalation into the lungs of the user.

BACKGROUND OF THE INVENTION

Telescoping and pivoting joints have been known in the art, for example in the design of aerosol medicament dispensers.

Various types of aerosol medicament dispensers, useful for the treatment of bronchial and other ailments, are constructed to be retractable into a compact storage unit. In its retracted position, the dispenser may be more conveniently stored, for example, in a purse or pocket.

Compact retractable aerosol dispensers are well known in this field, and an example of this type of dispenser is disclosed in U.S. Pat. No. 3,184,115. In order to protect the dispenser from dirt, grime or other external contamination, a protective sleeve can be incorporated into the design of the dispenser, the sleeve functioning also as a deceleration chamber and mouthpiece.

The sleeve-deceleration chamber may be telescopically extended from the main body of the dispenser, and then pivoted about the spray nozzle so that it projects outwardly at a right angle from the dispenser body. This kind of perpendicular orientation between the sleeve and the dispenser body, which carries an aerosol container, has proven to be easily and conveniently operated with a single hand, for the dispensing of medicament. Examples of medicament dispensers having the features discussed above are shown in U.S. Pat. Nos. 3,994,421 and 3,927,806. U.S. Pat. Nos. 3,184,115, 3,927,806 and 3,994,421 are hereby incorporated by reference, and illustrate two types of construction for this kind of dispenser, and how the dispensers are operated.

Dispensers of medicament of the type herein referred to must be capable of convenient use by persons who are ill and in a state of discomfort or actually physically impaired. The dispenser must be simple to operate, and easily shifted between the operating and storage configurations. A design prerequisite for a dispenser having a pivoting sleeve is that the sleeve must not be pivoted in a direction which does not bring it into alignment with the spray nozzle. If the sleeve is capable of being pivoted in the wrong direction, medicament will not be properly dispensed, perhaps when the patient needs it the most. At the very least, this constitutes an annoying frustration for the user.

An additional potential difficulty with retractable dispensers of this type is that it is possible for the sleeve to be separated from the dispenser housing, because of a poor interconnection between the two, so that the device may easily fall apart. The present invention solves these problems in a way which provides a dispenser which is easy to use, reliable, of simple construction and easily assembled.

SUMMARY OF THE INVENTION AND OBJECTS

An objective of the invention is the provision of a joint between a pair of tubular members which allows the members to telescopically shift in position and to pivot, but said joint preventing any pivoting movement of the members in an undesired direction.

An important feature of the invention involves the provision of a simplified and highly reliable novel interconnection between the sleeve serving as deceleration chamber and inhaler and the housing for an aerosol container, of a retractable articulated medicament spray dispenser.

A more specific objective of the invention is the provision in a dispenser of the kind described, of an improved sliding pin and stud interconnection which prevents the sleeve from pivoting in any direction other than the direction required to bring the dispenser into an operating configuration.

A more particular objective of the invention is the provision in a two piece articulated dispenser of a pair of projecting pin-like elements connected to a sleeve-like inhaler which may be snapped into corresponding slots in a dispenser housing, with the pin-like elements having studs shaped to be positively engaged within said slots.

Still another important objective of the invention is the simplification of manufacturing and assembly techniques for retractable dispensers.

In summary, the foregoing and various other objectives of the invention are achieved by the provision, in a retractable medicament spray dispenser comprised of a barrel like deceleration chamber hingedly slidably connected to a housing for an aerosol container, of a pair of interconnecting pin-like elements connected to the sleeve, and retained within a pair of parallel slots on the sides of the dispenser housing. At the inner end of each pin is a stud protruding perpendicularly to the pin, so that any pivoting movement of the sleeve about the axis of the pin causes a corresponding rotary movement of said stud. An abutting surface adjacent said slots cooperates with the protruding studs to prevent pivoting movement of the sleeve and its attached pins and studs, in any direction other than that direction which moves the sleeve to an operating configuration with respect to the housing.

The foregoing and other objectives and advantages of the invention will become apparent upon reference to the following detailed description of a preferred embodiment of the invention.

BRIEF DESCRIPTION OF THE DRAWINGS

In the Drawings:

FIG. 4 is a partial sectional side view similar to FIG. 3, but with the sleeve components and dispenser housing separated, and additionally showing an aerosol container of the type that may be used with the dispenser;

FIG. 5 is a top view of the sleeve body shown in FIG. 4;

FIG. 6 is a partial sectional view taken along line 6—6 of FIG. 3, showing the interconnection of the sleeve to the housing;

FIG. 7 is an enlarged sectional view of the joint shown in both FIG. 3 and FIG. 6;

FIG. 8 is an enlarged sectional view of the joint of the preferred embodiment as seen along line 8—8 of FIG. 2;

FIG. 9 is an enlarged sectional view of the joint as seen along line 9—9 of FIG. 1; and FIG. 10 is an enlarged pictorial view of one of the joints shown in FIG. 6, as seen from the interior of the dispenser housing.

DETAILED DESCRIPTION OF A PREFERRED EMBODIMENT

Figure 1:
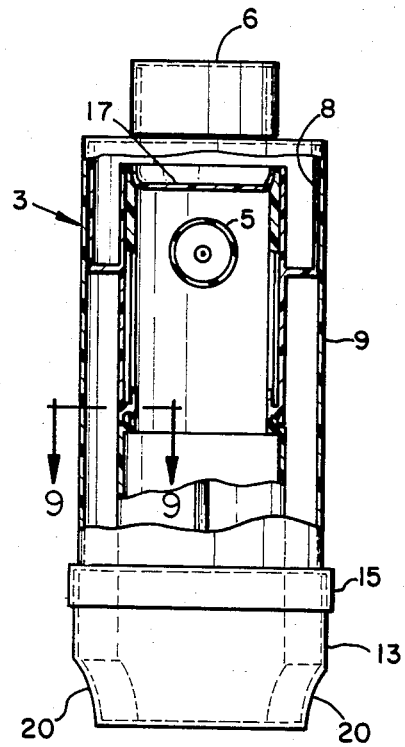
FIG. 1 is a partial sectional front view of a preferred embodiment of the retractable medicament spray dispenser of the invention, in its fully retracted configuration.
Figure 2:
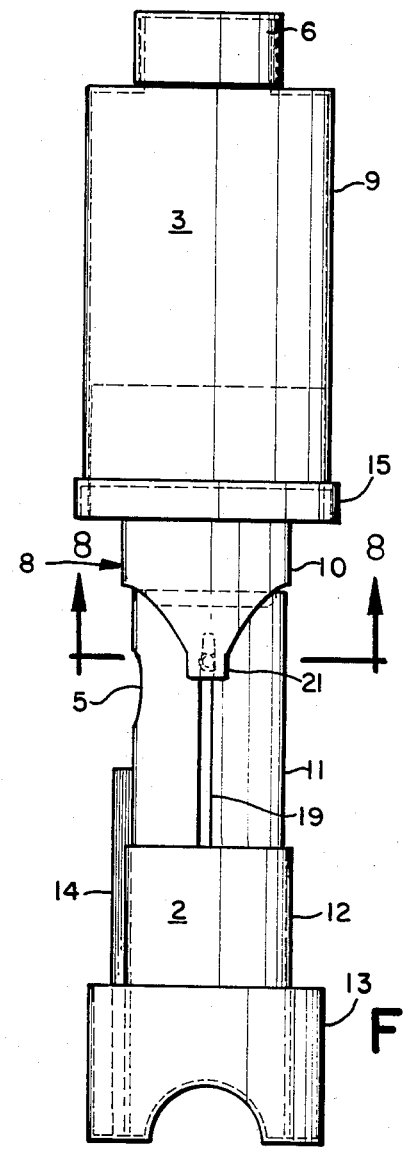
FIG. 2 is a side view of the dispenser of FIG. 1 showing the sleeve means in a fully extended configuration.
Figure 3:
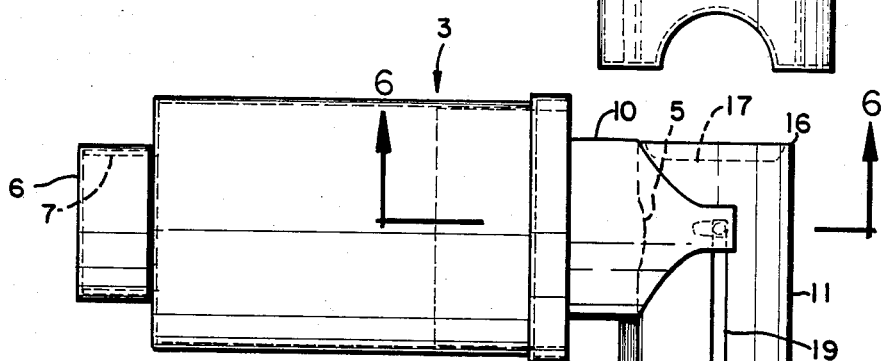
FIG. 3 is a side view of the dispenser of FIG. 1 with the sleeve means in an operating configuration wherein it is telescoped and pivoted perpendicularly to the dispenser housing.

Reference is first made to FIGS. 1-4 for a general discussion of features of a preferred form of the invention. A retractable medicament spray dispenser is shown with the parts arranged in three different configurations, including the storage configuration seen in FIG. 1, an extended or telescoped configuration in FIG. 2, and an operating configuration as seen in FIG. 3. The dispenser includes a hollow cylindrical housing 2 and a cylindrical sleeve means 3. The end of sleeve means 3 is provided with a mouthpiece which is covered with a cap 6. An aerosol container 4, shown in broken lines in FIG. 4, is intended to be inserted axially into housing 2, and is preferably frictionally held in position within the housing. The aerosol container 4 has a valve 4a through which aerosol spray is directed by way of passageway 18 into a nozzle 5 extending radially outwardly through the side wall of the housing when the bottom of the dispenser is pushed upwardly as the parts are illustrated in FIG. 4.

In the storage configuration, the dispenser parts are fully retracted and sealed against contamination from external dust, dirt or other extraneous matter. Sleeve means 3 and cap 6 function cooperatively, along with housing base portion 13, as a protective container for those parts of the dispenser which deliver the medicament to the patient.

When it is desired to use the dispenser, sleeve means 3 and housing 2 are pulled apart until they are telescopically shifted to the configuration seen in FIG. 2. As viewed in FIG. 3, sleeve means 3 is then pivoted leftward, which is the direction which brings it into alignment with nozzle portion 5 in the sidewall of the housing 2. By the use of features to be described hereinbelow, the sleeve means 3 is only capable of being pivoted to the left as viewed in FIG. 3, which is the direction for dispensing. It is not possible for a patient or other user to mistakenly rotate sleeve means 3 in a direction in which the nozzle is not in alignment with sleeve 3.

After sleeve 3 has been pivoted to the dispensing configuration of FIG. 3, cap 6 is removed from the mouthpiece 7. The aerosol container 4 containing a desired medicament is inserted in housing 2, if this had not already been done. The mouth is cupped over the mouthpiece 7, and aerosol container 4 is actuated, preferably by pushing it axially upwardly or inwardly relative to housing 2, thus spraying a measured dose of medicament through nozzle 5, into sleeve means 3. Sleeve means 3 acts as a deceleration chamber and mouthpiece, and permits the user to inhale an appropriate dosage of aerosolized medicament through the opening or mouthpiece 7.

Referring particularly to FIG. 4, the sleeve means generally described above and indicated by the reference character 3 is preferably of two-piece construction comprising an elongated tubular barrel 9 and a second tubular shaped part generally indicated at 8. Part 8 has a first tubular section 8a dimensioned to slidably interfit within the tubular barrel 9 and a reduced diameter sleeve portion 10.

A mouthpiece 7 extends from one end of the tubular barrel 9. Cap 6 fits over mouthpiece 7 when the dispenser is not in use.

Sleeve portion 10 carries a pair of depending ears 21 on each of which is mounted an inwardly facing pin-like projection 22. The inner end of each projection 22 is provided with a head or stud 23, shown in enlarged form in FIGS. 7-10. As can be seen from these figures, the studs 23 are substantially rectangular in form with the long dimension of each rectangle being parallel to the axis of the sleeve portion 10. For reasons to be explained hereinafter, the studs are preferably mounted off center on the pins so that they are closer to one end 23a than the other as is shown in FIG. 10.

Referring again to FIG. 4, housing 2 is comprised of a base section 13, and concentrically mounted intermediate and head sections identified as 12 and 11 respectively. Section 11 is provided with a pair of longitudinally extending slots 19 which extend through its sidewall on opposite sides thereof in parallel relationship. Slots 19 preferably extend from the upper edge of section 12 to a point just above the center line of nozzle 5.

To interconnect tubular part 8 to housing 2, the ears 21 are slightly expanded and fitted over the end of cylindrical head section 11 with the parts oriented coaxially as seen in FIG. 2. The studded projections are aligned with slots 19 and pressed inwardly so that they snap into place. In order to facilitate the fitting of the studded projections into the slots, the stud's inward facing surface 25 is preferably slightly narrower than the slot width, and the stud sides are preferably slightly inclined outwardly at its bottom as shown at 24 in FIG. 8. In pressing the ears 21 relatively inwardly, the studs wedge through the slots with temporary resilient deformation of stud and slot. Once a stud 23 has passed through the slot it is retained within the slot, due to the greater width of the bottom of the stud relative to the slot 19.

With studs 23 securely retained in slots 19, sleeve portion 10 of the sleeve 3 is free to slide between the telescoped position shown in FIG. 2 and the retracted position shown in FIG. 1. Since slot 19 has a constant width throughout its length, in the preferred embodiment shown, stud 23 is retained at all points along the slot. In order that this sliding motion not be obstructed, it is important that studs 23 do not impinge upon the aerosol container 4, which is kept within housing 2. To avoid this problem, head section 11 has an indented surface on the inward side adjacent slot 19, so that studs 23 are recessed relative to interior surface 26 as is shown in FIG. 9. Preferably, studs 23 should remain recessed in the interior surface 26 of head section 11 for at least that part of section 11 where the aerosol container may interfere with their movement. (See FIG. 4).

A stud 23 at the upper extremity of slot 19 is seen in FIG. 10 from inside housing 2, with an abutment or abutting surface 27 on one side of projection 22 to prevent stud 23 from pivoting in the clockwise direction. Stud 23 may only pivot in the direction of arrow a, which corresponds to the direction of pivoting sleeve means 3 into alignment with nozzle 5. Abutment 27 thus comprises a stop means which ensures that sleeve 3 can only pivot from the extended configuration of FIG. 2 in a direction bringing it into alignment with spray nozzle 5, while preventing it from pivoting in the opposite incorrect direction.

Preferably the elongated stud 23 should be parallel to the longitudinal axis of sleeve means 3. As shown in FIG. 2, when sleeve means 3 has been pulled upward to the extended position and pin-like projection 22 is at the upper extremity of slot 19, the stud 23 projects upwardly beyond slot 19, so that stud 23 makes an interlocking with the interior surface of head section 11 throughout a large part of stud 23. During the rotation of sleeve means 3 to and from the dispensing position, whereupon the inward facing surfaces of ears 21 frictionally slide upon upper ridge 16 resulting in some flexing and distortion of the ears 21, the stud 23 continues to make an interlocking contact with head section 11, and is securely retained therewithin.

When the members are fully rotated to the dispensing configuration shown in FIG. 3, the curved surfaces 10a of sleeve portion 10 make a substantially full contact with the cylindrical surface of upper housing portion 11 to exclude external matter from entering interiorly of sleeve means 3 or into the region of the nozzle 5 during use of the dispenser. Upper ridge 16 is preferably circular and flat, with upper recessed surface 17 also being circular and substantially flat. The preferred shape of upper ridge 16 and upper recessed surface 17 permit the housing to be conveniently grasped and steadied, for example, with the index finger placed over upper ridge 16 and into upper recessed surface 17. This shape also simplifies molding of the dispenser housing 2.

In the dispensing configuration of FIG. 3, sleeve means 3 is prevented from sliding from the position of coaxial alignment with nozzle 5 by means of an abutting fin 14 which extends outwardly from sections 11 and 12 of housing 2 and which contacts the lower surface of sleeve portion 10.

After use, cap 6 should be replaced to again seal off the interior space of sleeve 3 from external contaminants. Dispenser 2 is then collapsed by first pivoting sleeve 3 upwardly into the configuration of FIG. 2, and then pushing it downwardly relative to housing 2 until sleeve portion 10 contacts intermediate section 12, and enlarged ridge 15 contacts and engages base section 13, thereby obtaining the compact storage configuration of FIG. 1. Aerosol container 4 may be permanently stored within housing 2, and replaced only when the medication contained therein has been exhausted.

Although the preferred embodiment described is an aerosol medicament dispenser, it is seen that housing 2 and sleeve means 3 can be any two coaxially telescopically mounted tubular members. The slots 19 may be provided on either the inner or outer member, with the pin-like projection 22 provided on the other member. Furthermore, it would be possible to provide just a single joint comprising the slot and studded projection, or a pair of coaxial joints as shown in the preferred embodiment.

It will be obvious to those skilled in this field that the medicament dispenser and the sliding and pivoting joint of the invention may be subject to many modifications. Although the invention has been described in detail by reference to a preferred embodiment, it is recognized that other embodiments incorporating numerous modifications are possible within the scope of the invention claimed.

I claim:

1. A medicament spray dispenser for dispensing from an aerosol medicament container having a valve actuable to dispense a measured dose of medicament in aerosol form, comprising:

an elongated housing for holding and at least partially enclosing said container;

nozzle means at one end of the housing including a passageway connected to said valve, said nozzle means further including a spray nozzle leading from said passageway and pointing outwardly of said housing on an axis extending transverse to the long axis thereof;

a hollow open-ended sleeve telescopically mounted on said housing for longitudinal sliding motion between a retracted position overlying said spray nozzle and an extended position in which at least a major portion of said sleeve extends beyond the nozzle end of the housing;

joint means interconnecting the sleeve and the housing for relative sliding and pivotal movement, said joint means comprising a pair of oppositely disposed pins affixed to and projecting inwardly from the side surfaces of the sleeve, said housing having on its side wall a pair of oppositely disposed longitudinal slots equidistantly disposed from the axis of the spray nozzle, said slots extending to points adjacent the axis of the spray nozzle for receiving said pins, elongated studs attached to the inward end of each said pin, said elongated studs extending perpendicularly to each said pin, each said elongated stud being rigidly fixed relative to said sleeve, said sleeve when in the extended position being rotatable from a position of coaxial alignment with the long axis of the housing, each said stud being elongated in a direction extending lengthwise of its slot when said sleeve is in said position of coaxial alignment with said housing whereby a substantial surface area of each stud underlies the housing side wall adjacent to the end of the slot when the sleeve is in the extended position thereby interlocking the sleeve and the body against accidental separation during rotation of the sleeve from the position of coaxial alignment;

and abutment means positioned adjacent the studs to block rotation of said studs and said sleeve from the position of coaxial alignment in a direction away from the position of alignment with the spray nozzle.

2. A dispenser as defined in claim 1 wherein each said slot on the housing side wall has a constant width along the entire length thereof, said elongated studs having an overall width dimension slightly greater than the width dimension of the slots, each said stud having an inward facing surface slightly narrower than the width dimension of the slot, and a bevelled side surface inclined outwardly towards said pin, each said stud being forceably engageable into said slot by a sliding contact between the bevelled side surface and the slot.

3. A dispenser as defined in claim 2 wherein said stud projects substantially beyond the end of said slot when the sleeve is in said extended position in said position of coaxial alignment with said housing.

4. Apparatus according to claim 2 wherein each said elongated stud is joined to its said pin on a point on its longitudinal axis offset from its center.

5. A dispenser as defined in claim 1 wherein said stop means and housing are molded integrally of a resilient plastic material.

* * * * *